US006936002B2

(12) United States Patent
Kochamba et al.

(10) Patent No.: US 6,936,002 B2
(45) Date of Patent: *Aug. 30, 2005

(54) STABILIZING TISSUE METHOD AND APPARATUS

(75) Inventors: Gary S. Kochamba, Studio City, CA (US); Suzanne E. Kochamba, Studio City, CA (US)

(73) Assignee: Kochamba Family Trust, Studio City, CA (US)

( * ) Notice: Subject to any disclaimer, the term of this patent is extended or adjusted under 35 U.S.C. 154(b) by 18 days.

This patent is subject to a terminal disclaimer.

(21) Appl. No.: 10/387,745

(22) Filed: Mar. 12, 2003

(65) Prior Publication Data

US 2004/0181120 A1 Sep. 16, 2004

Related U.S. Application Data

(63) Continuation of application No. 09/268,556, filed on Mar. 15, 1999, now Pat. No. 6,607,479, which is a continuation-in-part of application No. 09/042,853, filed on Mar. 17, 1998, now Pat. No. 6,251,065.

(51) Int. Cl.[7] .......................... A61B 19/00; A61F 13/00
(52) U.S. Cl. ..................................................... 600/37
(58) Field of Search .................. 600/37, 201, 204–206, 600/208, 210, 218, 227, 228, 229, 231, 233, 235, 237

(56) References Cited

U.S. PATENT DOCUMENTS

| 3,745,998 | A | 7/1973 | Rose ......................... 128/89 R |
| 3,762,404 | A | 10/1973 | Sakita |
| 4,299,213 | A | 11/1981 | Violet |
| 4,447,227 | A | 5/1984 | Kotsanis |
| 4,657,003 | A | 4/1987 | Wirtz |
| 5,159,921 | A | 11/1992 | Hoover |
| 5,290,082 | A | 3/1994 | Palmer et al. |
| 5,695,514 | A | 12/1997 | Chin .......................... 606/190 |
| 5,727,569 | A | 3/1998 | Benetti et al. .............. 128/898 |

(Continued)

OTHER PUBLICATIONS

Borst et al.; "Coronary Artery Bypass Grafting Without Cardiopulmonary Bypass and Without Interruption of Native Coronary Flow Using a Novel Anastomosis Site Restraining Device ("'Octopus'");" JACC; vol. 27, No. 6; May 1996; pp. 1356–1364.

Jansen et al.; "Less Invasive Off–Pump CABG Using a Suction Device for Immobilization: The 'Octopus' Method;" European Journal of Cardio–Thoracic Surgery: vol. 12; 1997. pp. 406–412.

Octopus.TM; "Tissue Stabilizer and Accessory Products, Defining the Future of Minimally Invasive and Beating Heart Cardiac Surgery," Jan. 15, 1998; Medtronic Advertisement; Aug. 1997; The Annals of Thoracic Surgery.

*Primary Examiner*—Samuel G. Gilbert
(74) *Attorney, Agent, or Firm*—Greenberg Traurig, LLP; Christopher Darrow, Esq.

(57) ABSTRACT

A tissue stabilizer includes a pneumatic rigidifying bladder which is flexible when at ambient pressure and rigid when at negative pressure or evacuated. Structure such as straps with hook-and-eye fasteners attaches the rigidifying bladder to tissue to be stabilized, such as a broken arm. When positioned on the tissue, the bladder is evacuated, thereby rigidifying the bladder and supporting the tissue. The tissue stabilizer may be configured for use in surgical procedures, such as performing coronary artery bypass grafting (CABG) on a warm, beating heart. In a cardiac embodiment, the tissue stabilizer includes an attaching bladder with a plurality of openings. When suction is applied at a port of the attaching bladder, suction is applied at the openings, which is utilized to attach the stabilizer to the epicardium of the heart. Once in position on the heart, suction may be applied at a port of the rigidifying bladder. When rigid, the heart may be moved as desired to perform CABG procedures.

10 Claims, 12 Drawing Sheets

U.S. PATENT DOCUMENTS

| | | |
|---|---|---|
| 5,782,746 A | 7/1998 | Wright ............... 600/37 |
| 5,807,243 A | 9/1998 | Vierra et al. ............ 600/204 |
| 5,836,311 A | 11/1998 | Borst et al. ............ 128/897 |
| 5,865,730 A | 2/1999 | Fox et al. ............... 600/228 |
| 5,868,763 A | 2/1999 | Spence et al. ........... 606/153 |
| 5,894,843 A | 4/1999 | Benetti et al. |
| 5,921,979 A | 7/1999 | Kovac et al. ............ 606/213 |
| 5,927,284 A | 7/1999 | Borst et al. ............ 128/898 |
| 5,957,835 A | 9/1999 | Anderson et al. ........ 600/201 |
| 5,976,069 A | 11/1999 | Navia et al. ............ 600/37 |
| 5,984,864 A | 11/1999 | Fox et al. |
| 6,007,486 A | 12/1999 | Hunt et al. |
| 6,015,378 A | 1/2000 | Borst et al. |
| 6,019,722 A | 2/2000 | Spence et al. ........... 600/210 |
| 6,032,672 A | 3/2000 | Taylor |
| 6,036,641 A * | 3/2000 | Taylor et al. ............ 600/231 |
| 6,050,266 A | 4/2000 | Benetti et al. |
| 6,066,107 A | 5/2000 | Habermeyer |
| 6,193,652 B1 | 2/2001 | Berky et al. |
| 6,206,827 B1 | 3/2001 | Chin et al. ............ 600/217 |
| 6,328,688 B1 | 12/2001 | Borst et al. |
| 6,334,843 B1 | 1/2002 | Borst et al. |
| 6,336,898 B1 | 1/2002 | Borst et al. |
| 6,338,712 B2 * | 1/2002 | Spence et al. ........... 600/201 |
| 6,346,077 B1 | 2/2002 | Taylor et al. |
| 6,350,229 B1 | 2/2002 | Borst et al. |
| 6,364,826 B1 | 4/2002 | Borst et al. |
| 6,371,906 B1 | 4/2002 | Borst et al. |
| 6,394,948 B1 | 5/2002 | Borst et al. |
| 6,464,630 B1 | 10/2002 | Borst et al. |
| 6,506,149 B2 | 1/2003 | Peng et al. |
| 6,514,250 B1 | 2/2003 | Jahns et al. |

* cited by examiner

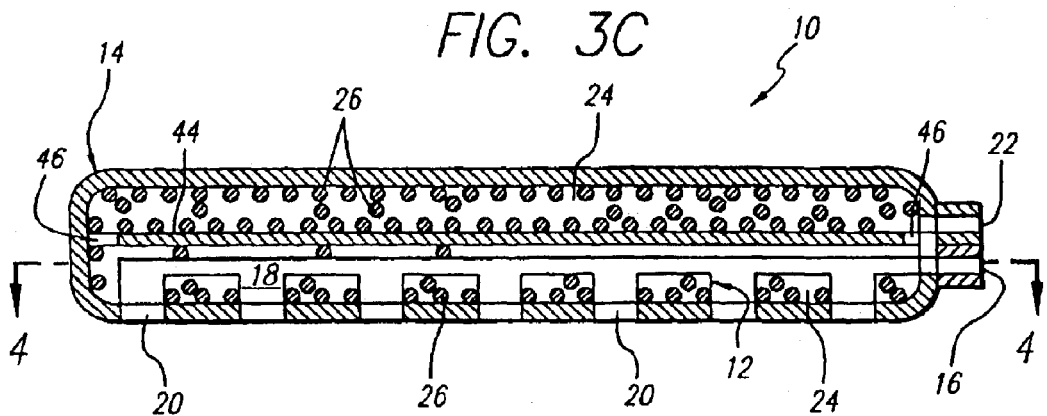
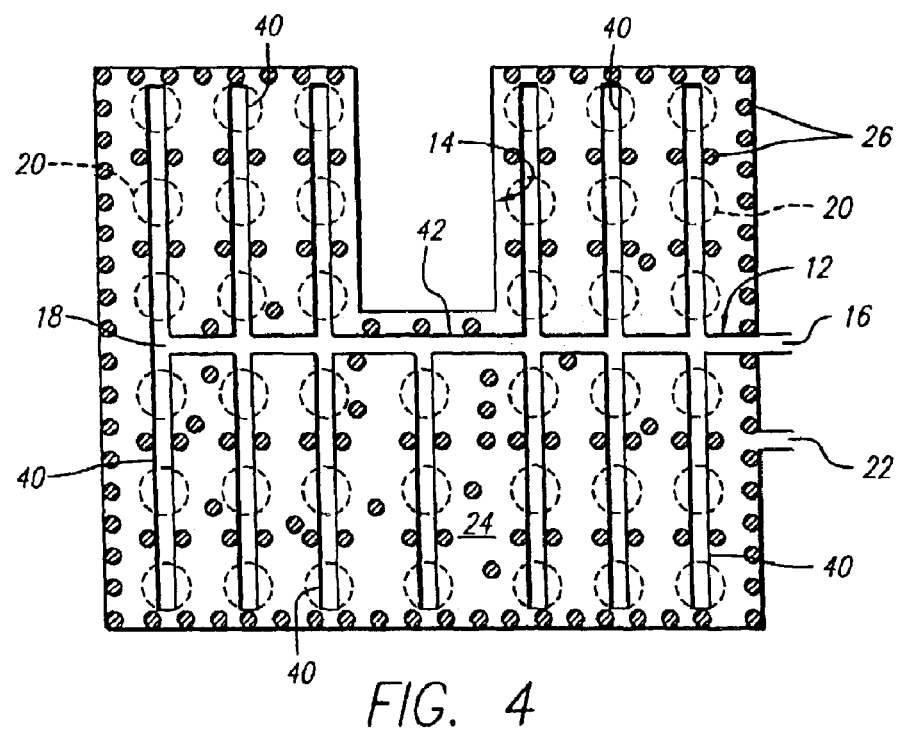

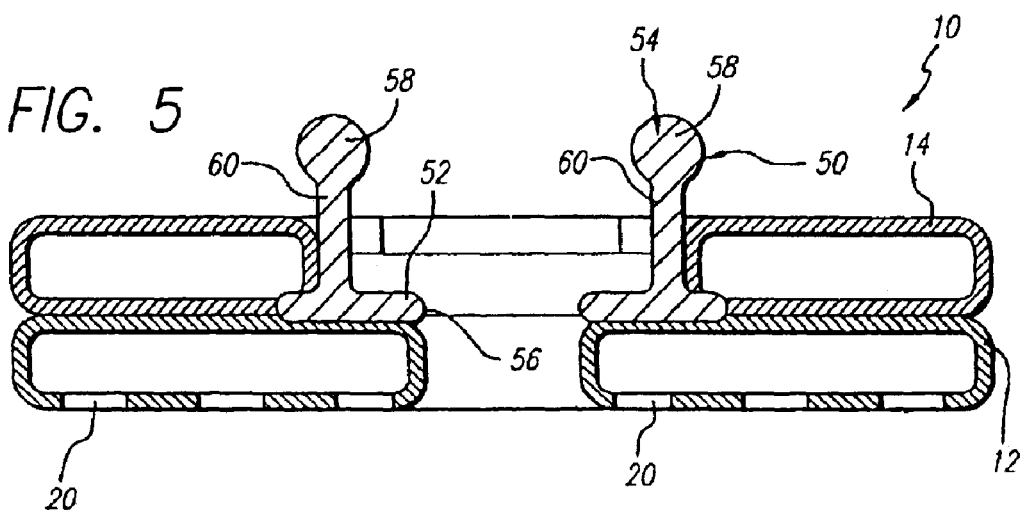
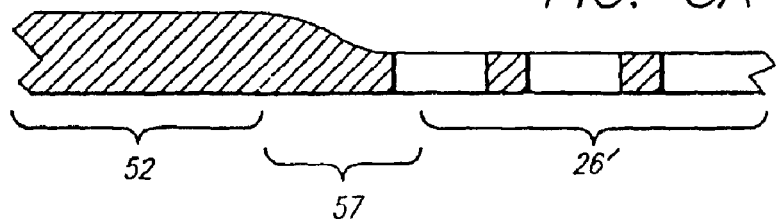
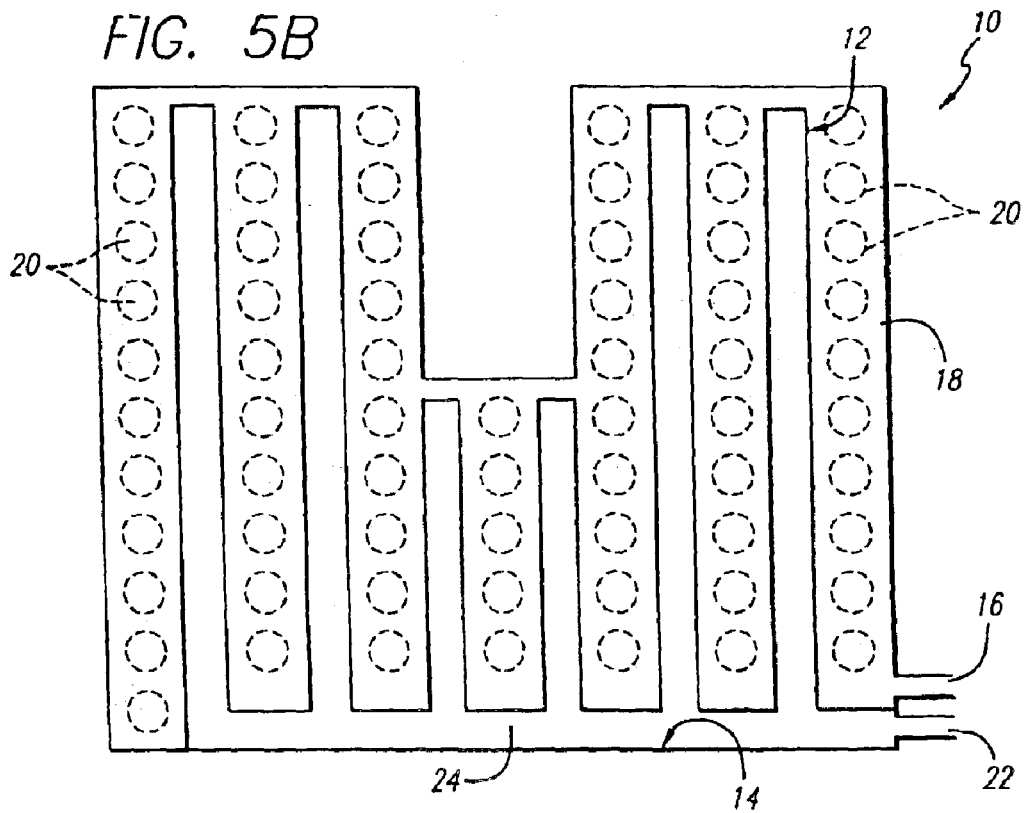

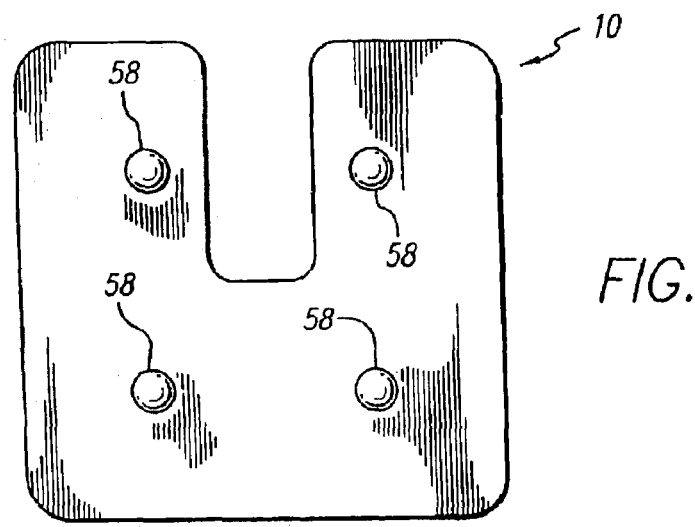
FIG. 6
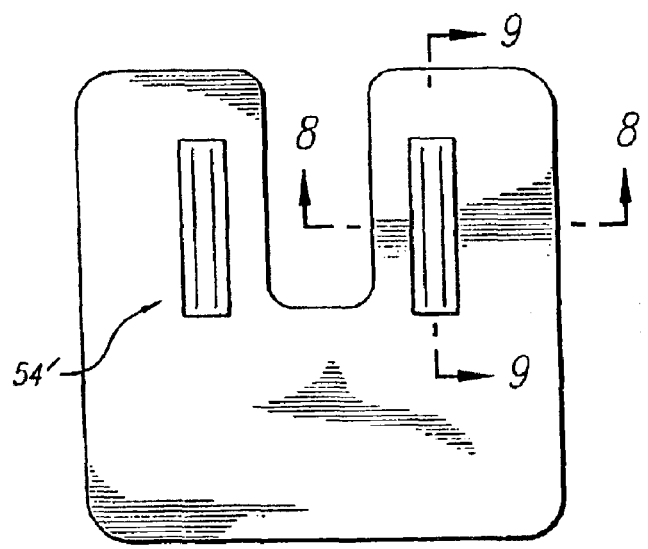
FIG. 7
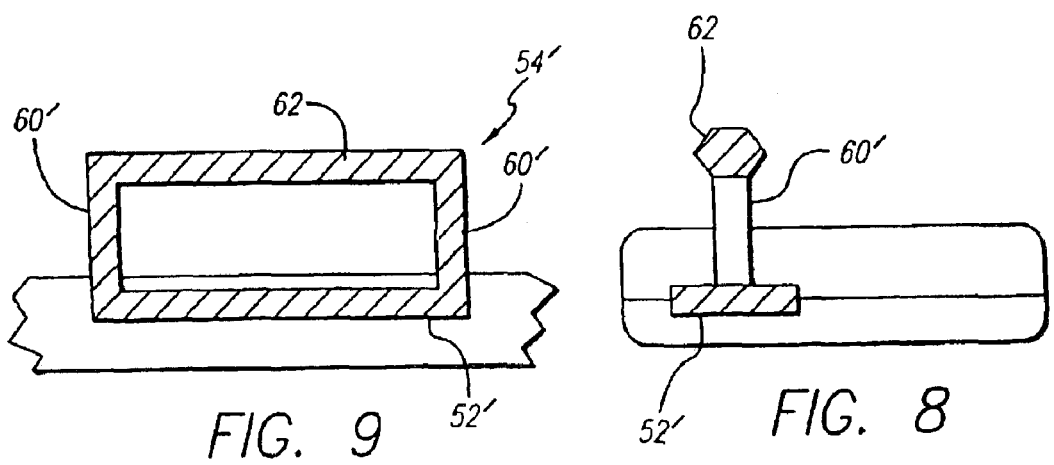
FIG. 9
FIG. 8

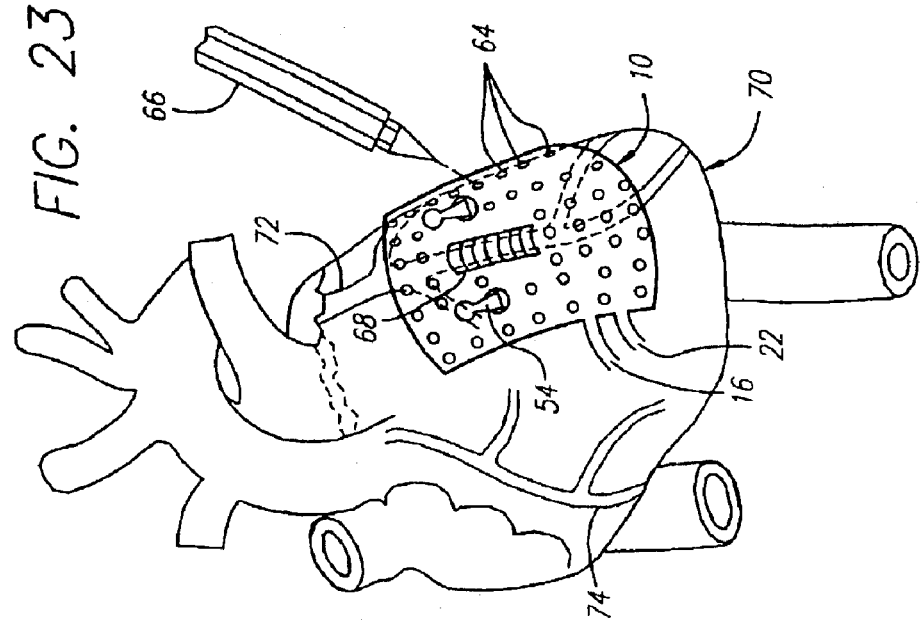
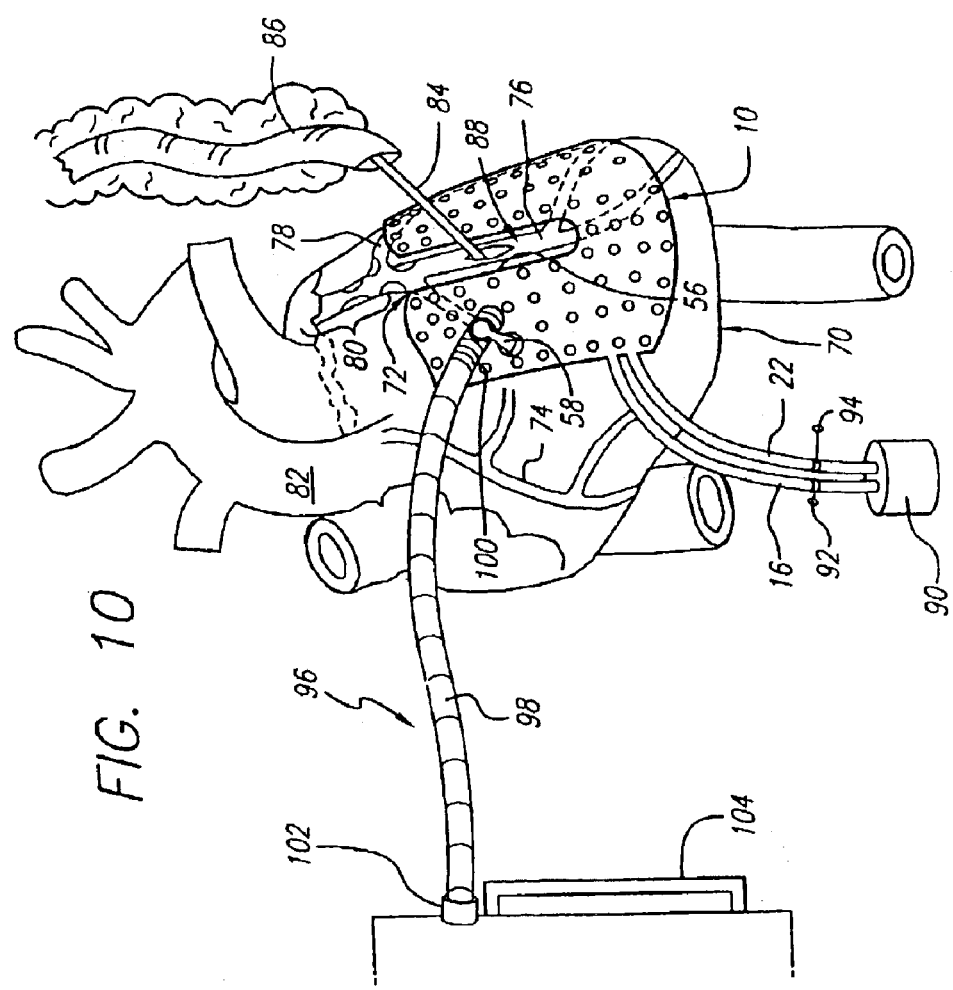

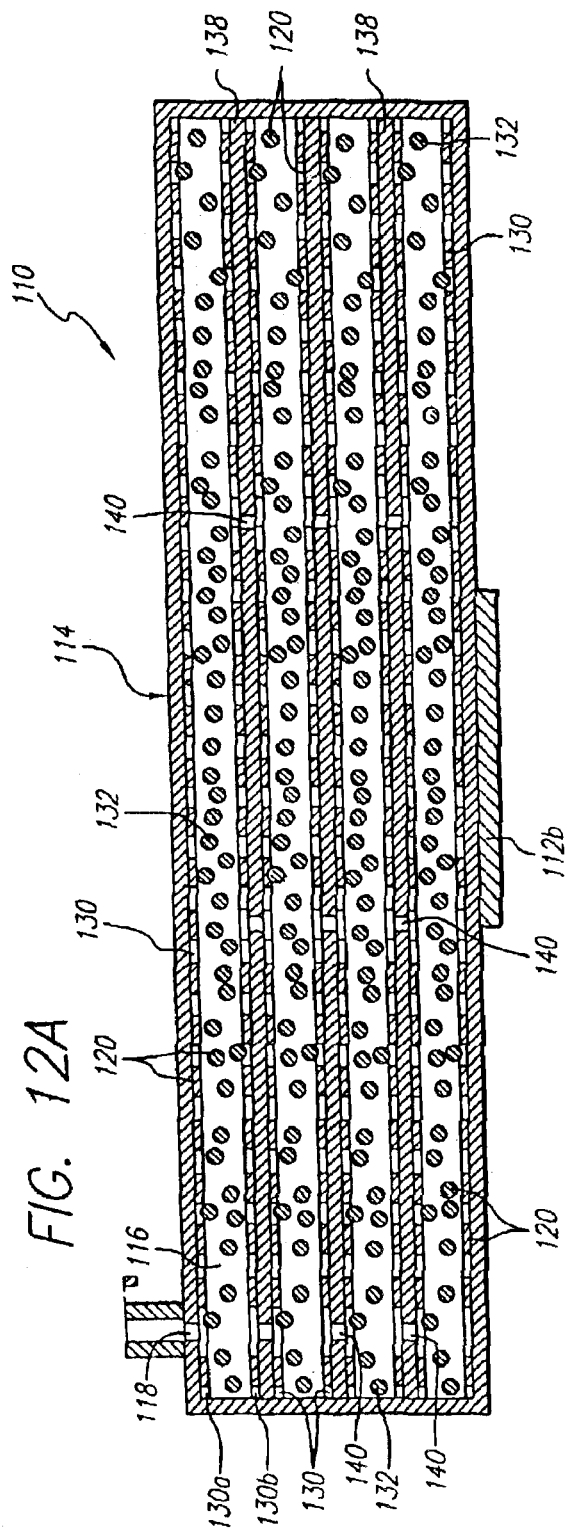
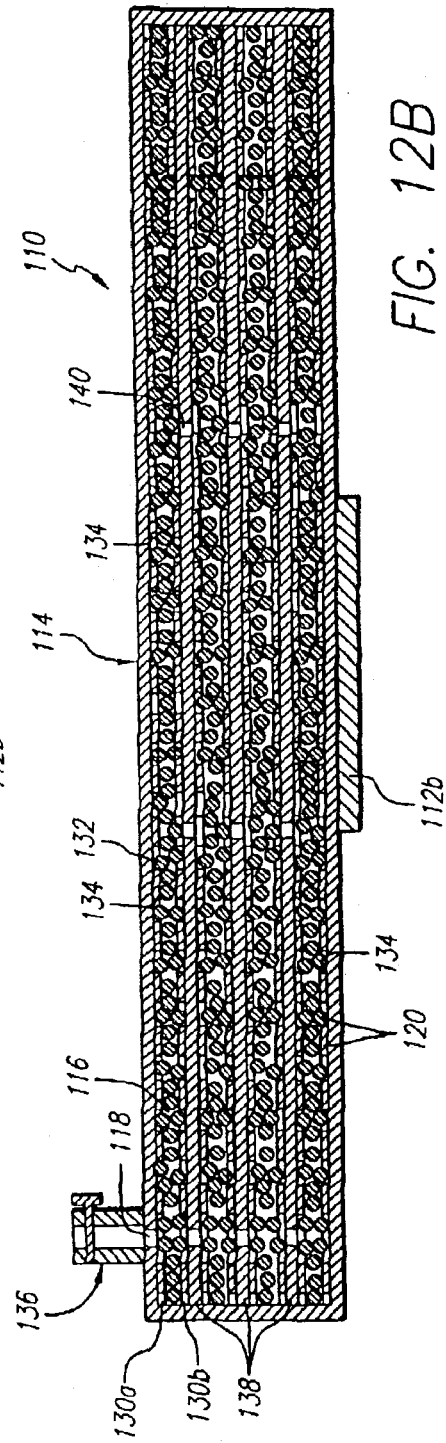

FIG. 13
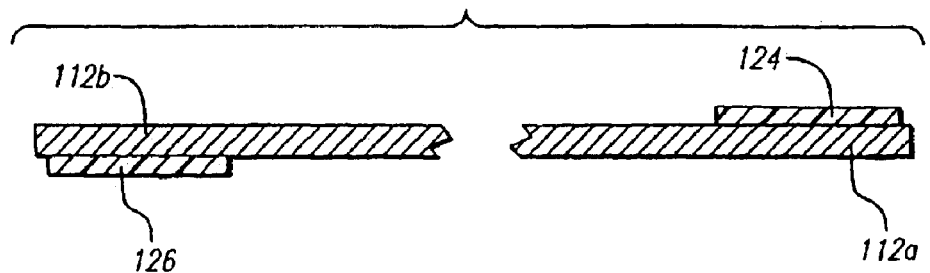
FIG. 14
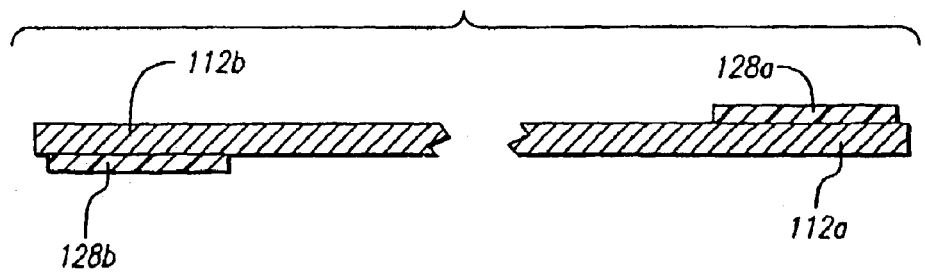
FIG. 17A
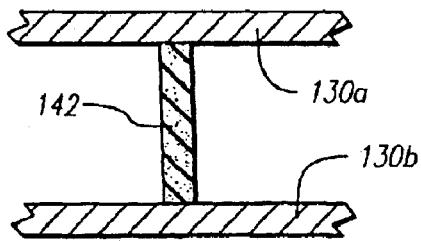
FIG. 17B
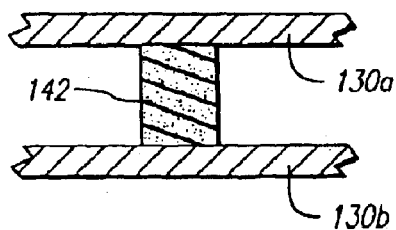
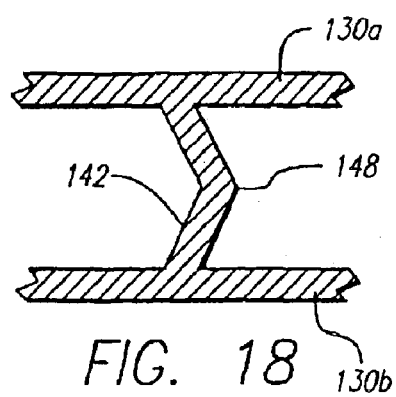
FIG. 18
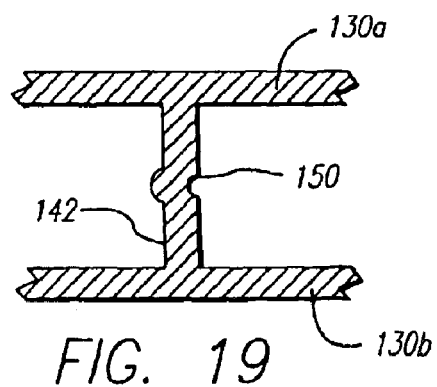
FIG. 19

STABILIZING TISSUE METHOD AND APPARATUS

RELATED APPLICATIONS

This application is a continuation of, and claims priority to U.S. patent application Ser. No. 09/268,556, entitled "Methods and Apparatus for Stabilizing Tissue", now U.S. Pat. No. 6,607,479, filed on Mar. 15, 1999, which is a continuation-in-part of U.S. patent application Ser. No. 09/042,853, entitled "Methods and apparatus for stabilizing tissue", which is now U.S. Pat. No. 6,251,065, filed on Mar. 17, 1998 and issued on Jun. 26, 2001, which are both herein incorporated by reference in their entirety.

FIELD OF THE INVENTION

The present invention relates in general to devices for stabilizing tissue and to methods for using such tissue-stabilizing devices, particularly cardiac tissue stabilizers. More particularly, the present invention relates to medical devices designed to stabilize the heart, for example, to retain the heart physically in an stabile position, during cardiac surgery. The apparatus of the present invention allows a surgeon to perform cardiac surgery on a warm beating heart, thus eliminating the need to place a patient on a cardiac bypass machine to stop the heart from beating. The methods and apparatus of the invention are particularly useful when performing coronary artery bypass grafting procedures such as coronary anastomosis.

BACKGROUND OF THE INVENTION

There are many instances in which tissue needs stabilization. One common instance is in the case of broken bones. Broken bones need to be set and then held rigid and in a stabile position by a cast in order to heal properly. Sprained joints, such as sprained ankles, wrists, and fingers, also require tissue stabilization. In these cases, splints, tapes, and bandages are often used to maintain the joint in a relatively stabile position. Other instances include neck and spinal injuries.

In addition to these examples of external tissue stabilization, internal organs may also need to be stabilized for specific medical procedures. For example, the heart may need to be stabilized during cardiac procedures. One such procedures is coronary artery bypass graft surgery (CABG), which is the most commonly performed cardiac operation, accounting for over 80% of all cardiovascular surgery. Indeed, more than 400,000 CABG operations were performed in 1997 alone. The clinical spectrum of presenting problems resulting in consideration for CABG includes angina, unstable angina, congestive heart failure due to ischemia, myocardial infarction, survival of sudden cardiac death, and asymptomatic ischemia. In recent years, the profile of a typical CABG patient has expanded to include higher-risk patients, such as older patients and patients with more advanced stages of coronary artery disease, as well as patients for "re-do" operations who have already had at least one CABG operation. The effect of these changes is reflected in the higher morbidity and mortality associated with these higher-risk patients.

One of the risks involved in performing CABG is that the heart is stopped to provide a stabile operating platform. This is accomplished through the use of catheters, a heart-lung machine, and cardioplegia. After the procedure has been finished, the heart needs to be defibrillated. Risks involved in stopping the heart include damage from the catheters such as in the creation of thrombi and the possibility that the heart will not defibrillate.

In recent years, advances have been made so that the heart does not need to be stopped in order to perform CABG procedures, allowing CABG to be performed on a warm, beating heart. To do so, a relatively stabile operating platform needs to be maintained. Conventional apparatus developed to provide a stabile operating platform include devices which apply pressure against the heart and devices with a finger-shaped configuration which adhere to the heart through suction. To apply these devices to the heart, it takes both of the surgeons hands to position the devices on the heart. In addition, the devices do not establish secure contact with the epicardium of the heart and often need to be repositioned during the CABG procedure, which is time consuming and a nuisance.

In view of the foregoing, one of the objectives of the present invention is to provide methods and apparatus for stabilizing tissue which overcome the drawbacks of conventional techniques.

It is another object of the present invention to provide methods and apparatus for stabilizing a heart during cardiac procedures, particularly a warm, beating heart.

It is yet another object of the present invention to provide methods and apparatus for stabilizing tissue which may be applied at remote locations.

It is still another object of the present invention to provide methods and apparatus for stabilizing tissue with pneumatics.

INVENTION SUMMARY

These and other objects are achieved by the tissue stabilizers of the present invention and the method for their use which stabilize tissue through the use of pneumatics. In accordance with broad, functional aspects of the present invention, the tissue stabilizer of the invention includes a bladder which is substantially flexible when at ambient pressure. However, when subject to negative pressure, such as through suction or vacuum, the bladder becomes substantially rigid. Because of these features, in use the tissue stabilizer may be positioned on tissue to be stabilized by, for example, wrapping the stabilizer around the tissue in the case of an arm, or contouring the stabilizer to the surface topography of the tissue in the case of a heart. When in a desired position, the rigidifying bladder may be subject to negative pressure, thereby rigidifying the tissue stabilizer. When rigid, the tissue stabilizer maintains the tissue in a stable position. The tissue stabilizer is particularly useful when configured for performing coronary artery bypass procedures (CABG) on a warm, beating heart.

In accordance with one aspect of the present invention, a tissue stabilizer includes a flexible rigidifying bladder and means for attaching the rigidifying bladder to tissue to be stabilized, such as straps with hook-and-eye fasteners. The rigidifying bladder includes a chamber, a port through which the chamber is evacuatable, and rigidifying structure disposed within the chamber. The rigidifying structure is configured to be substantially rigid when the chamber is evacuated. When the chamber is at ambient pressure, the rigidifying structure is substantially flexible to allow the stabilizer to be contoured to the tissue. The tissue stabilizer may include a valve for sealing the chamber when evacuated to maintain rigidity of the bladder.

The rigidifying structure may include opposing layers of mesh between which a plurality of movable beads are disposed. When the chamber is pneumatically evacuated, the rigidifying bladder collapses, thereby drawing the opposing layers of mesh together which, in turn, urges the beads together. The frictional forces between the beads and the mesh resist movement relative to each other, thereby providing rigidity. The rigidifying structure may include a plurality of walls which divide the inner chamber into a plurality of cells. The cells may be connected by air passages. The dividing walls prevent the migration of beads, thereby maintaining a substantially consistent distribution of beads and substantially consistent rigidity across the extent of the stabilizer.

The rigidifying bladder may also include a plurality of inner walls which separate the chamber into layers. The inner walls may includes air passages so that each of the layers is in pneumatic communication with each other. The rigidity of the rigidifying bladder is generally proportional to the number of layers. For example, in embodiments of the stabilizer configured to stabilize broken bones, the chamber may be divided into four or five layers, each of which includes a pair of opposing layers of mesh and a plurality of movable beads.

The tissue stabilizer of the present invention may be configured for many medical applications. For example, the tissue stabilizer may be configured as a portable neck brace for use by emergency medical teams for supporting and stabilizing an injured patient's neck. The stabilizer may serve as a cast or a splint for stabilizing a broken bone that has been set. The tissue stabilizer may also be configured for athletic applications, such as protective gear or ankle support. The tissue stabilizer of the present invention is particularly useful in stabilizing the heart during cardiac procedures.

In this regard, an alternative embodiment of the tissue stabilizer of the present invention for cardiac applications includes a flexible first bladder for attaching the cardiac stabilizer to the heart and a flexible second bladder for rigidifying the stabilizer. Both bladders include an inner chamber and a port through which the chamber may be evacuated. The first bladder includes a plurality of openings which apply suction in response to suction applied at the port thereof. The second bladder includes rigidifying structure which rigidifies in response to suction applied at the port thereof. The cardiac stabilizer may include retaining structure which may be engaged with an external support for retaining the tissue stabilizer in a desired position when rigid. The cardiac stabilizer may also include a window for providing access to a surgical site.

In using the cardiac stabilizer to perform surgery, after providing access to the heart, the stabilizer is placed on the epicardium of the heart at a desired location, preferably with the window positioned over the surgical site. Suction is then applied at the port of the attaching bladder, thereby attaching the stabilizer to the heart. Suction then applied at the port of the rigidifying bladder, thereby rigidifying the cardiac stabilizer. A coronary artery bypass procedure may then be performed on the heart.

One of the advantages of the present invention is that the cardiac stabilizer may be contoured to the surface topography of the heart. This allows the attaching bladder to make secure contact with the heart, particularly when the heart has not been placed on a bypass machine (e.g., a heart-lung machine) but is warm and beating. The contouring allows the warm heart to be securely retained by the stabilizer, allowing the heart to be moved from the cardiac anatomical position to an anastomosis position. This is particularly advantageous when performing a bypass procedure on the circumflex branch of the left coronary artery. When the heart has been moved into an anastomosis position, the retaining structure of the cardiac stabilizer may be attached to external support structure to retain the heart in the anastomosis position.

One of the advantages of the invention is that the tissue stabilizer may be disengaged from the external support structure, de-rigidified, and detached from the tissue. This allows the stabilizer to be repositioned and then re-rigidified. In cardiac applications, such as on warm, beating hearts, the cardiac stabilizer may be disengaged from the external support, allowing the heart to be returned to the cardiac anatomical position if the heart should experience hemodynamic instability. When the heart regains stability, the heart may be repositioned in the anastomosis position and re-engaged with the external support.

Other objects, features, and advantages of the present invention will become apparent to those skilled in the art from a consideration of the following detailed description taken in conjunction with the accompanying drawings which illustrate, by way of example, the principles of the present invention in the context of a cardiac tissue stabilizer but which are equally relevant to stabilizers for supporting other types of tissue.

BRIEF DESCRIPTION OF THE DRAWINGS

FIG. 3A' is view similar to that of FIG. 3A, particularly illustrating the rigidifying bladder with applied suction;

FIG. 3C is a cross-sectional view of the cardiac stabilizer taken along line 3—3 of FIG. 1, illustrating yet another alternative embodiment of the stabilizer;

FIG. 4 is a cross-sectional view of the cardiac stabilizer taken along line 4—4 of FIG. 3C;

FIG. 5 is a cross-sectional view of the cardiac stabilizer taken along line 5—5 of FIG. 1;

FIG. 5A is an enlarged fragmentary cross-sectional view of a rigid plate and rigidifying structure of the invention;

FIG. 5B is a cross-sectional view of a rigidifying structure of the invention.

FIG. 6 is a plan view of the cardiac stabilizer, particularly illustrating an exemplary embodiment of engaging structure of the invention;

FIG. 7 is a plan view of the cardiac stabilizer, illustrating an alternative embodiment of the engaging structure of the invention;

FIG. 8 is a cross-sectional view of the cardiac stabilizer taken along line 8—8 of FIG. 7;

FIG. 9 is a cross-sectional view of the cardiac stabilizer taken along line 9—9 of FIG. 7;

FIG. 10 is a schematic view of a tissue stabilizer of the present invention in use during a cardiac procedure on a heart;

FIG. 12A is a cross-sectional view of the tissue stabilizer taken along line 12—12 of FIG. 11, particularly illustrating the tissue stabilizer at ambient pressure;

FIG. 12B is view similar to that of FIG. 12A, particularly illustrating the tissue stabilizer at negative pressure;

FIG. 13 is a fragmentary cross-sectional view of attaching straps of the tissue stabilizer, particularly illustrating a pressure-sensitive adhesive embodiment;

FIG. 14 is a fragmentary cross-sectional view of an alternative embodiment of the attaching straps of the tissue stabilizer, particularly illustrating a cohesive adhesive embodiment;

FIG. 17A is a cross-sectional view of the exemplary rigidifying structure taken along line 17—17 of FIG. 16, particularly illustrating an embodiment of a dividing wall at ambient pressure;

FIG. 17B is a view similar to that of FIG. 17A, particularly illustrating the dividing wall at negative pressure;

FIG. 18 is a fragmentary cross-sectional view of another embodiment of a dividing wall of exemplary rigidifying structure of the invention;

FIG. 19 is a fragmentary cross-sectional view of yet another embodiment of a dividing wall of exemplary rigidifying structure of the invention;

FIG. 23 is a schematic view of a tissue stabilizer of the present invention in use during a cardiac procedure on a heart;

DETAILED DESCRIPTION OF THE PREFERRED EMBODIMENTS

Figure 1:
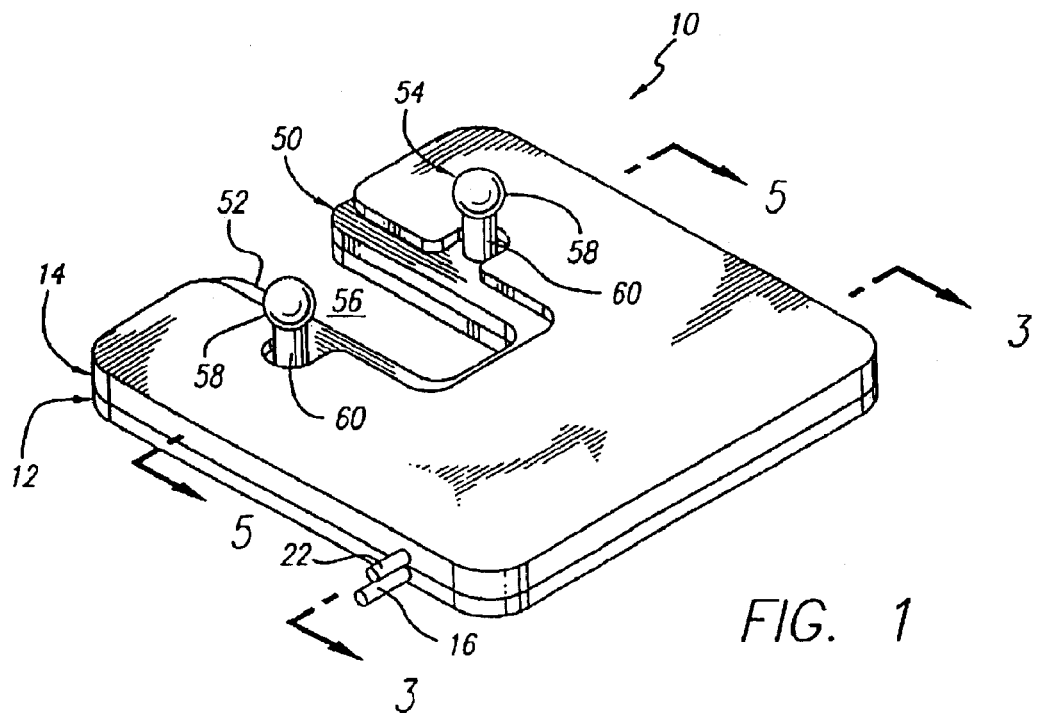
FIG. 1 is a perspective view of an exemplary tissue stabilizer configured as a cardiac stabilizer in accordance with the present invention, particularly illustrating a top surface of the stabilizer.
Figure 2:
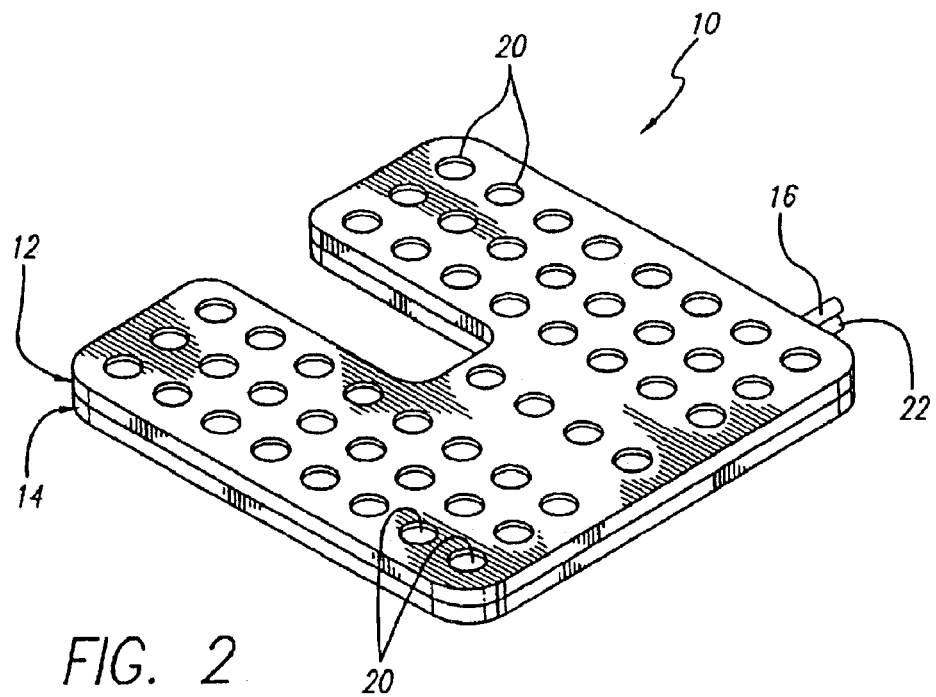
FIG. 2 is a perspective view of the cardiac stabilizer, particularly illustrating a bottom surface of the stabilizer.

Referring more particularly to the drawings, an exemplary tissue stabilizer 10 configured in accordance with the teachings of the present invention is illustrated in FIGS. 1 and 2. For descriptive purposes and without limiting the scope of the present invention, exemplary stabilizer 10 is illustrated as a cardiac stabilizer for stabilizing a heart during surgical procedures, particularly surgical procedures which are performed on a heart which is not immobilized but rather which is warm and beating. Tissue stabilizers configured for alternative functions are contemplated as being within the scope of the invention as will be understood by those skilled in the art. Those skilled in the art will also appreciated that exemplary tissue stabilizer 10 utilized during cardiac procedures must be biocompatible and possess substantially a traumatic features. However, these additional properties may not be essential to all tissue stabilizers produced in accordance with the teachings of the invention.

Exemplary tissue stabilizer 10 is substantially flexible and is conformable to the shape or anatomical topography of a particular piece or section of tissue, such as the epicardium of the left ventricle of a heart. Tissue stabilizer 10 is also attachable to tissue in a substantially a traumatic manner through, for example, the use of suction apparatus. Furthermore, stabilizer 10 may be rigidified to maintain a desired shape through the use of auxiliary suction apparatus. Each of these features of the present invention will be described in detail below.

Figure 3A:
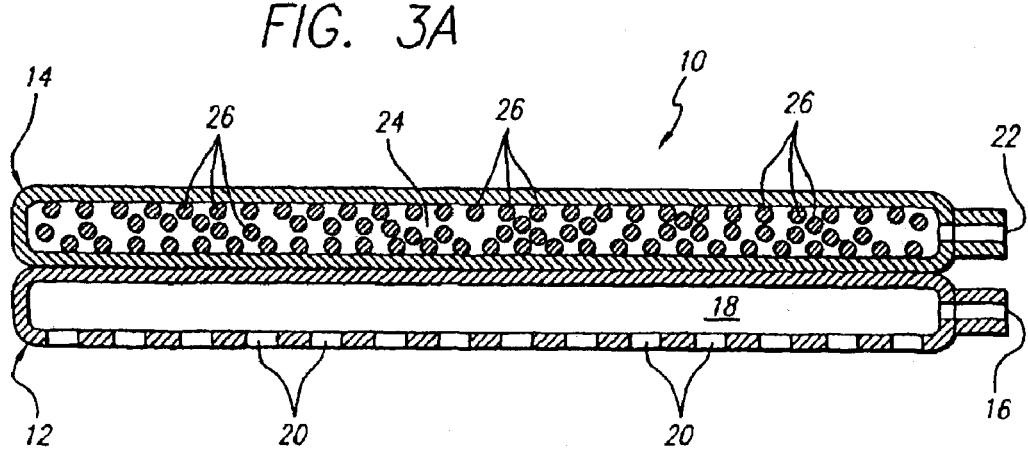
FIG. 3A is a cross-sectional view of the cardiac stabilizer taken along line 3—3 of FIG. 1, particularly illustrating a rigidifying bladder without applied suction.
Figure 3A:
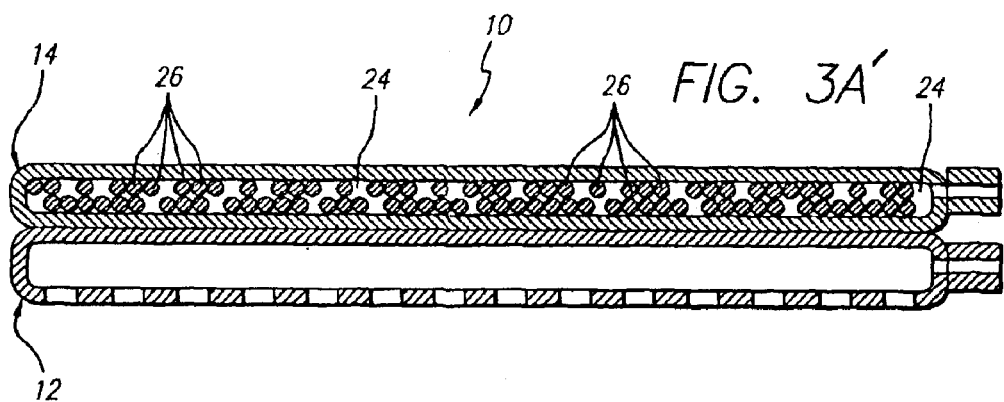

With additional reference to FIG. 3A, exemplary stabilizer 10 includes structure for attaching the stabilizer to tissue, such as an attaching bladder 12, and structure for becoming substantially rigid upon actuation, such as a rigidifying bladder 14. Attaching bladder 12 has a port 16 leading into an inner chamber 18 in which a plurality of openings 20 are formed. Exemplary bladder 12 is substantially flexible and configured so that openings 20 apply suction when suction is applied at port 16. Rigidifying bladder 14 has a port 22 leading into an inner chamber 24 in which rigidifying structure 26 is disposed. A portion of rigidifying structure 26 may be attached to bladder 14, and a portion of the rigidifying structure may be unattached or free floating. In FIG. 3A, free-floating rigidifying structure is exemplified in the figures by substantially spherical beads or balls, although any structured configured in accordance with the principles of the present invention may be utilized. In addition, rigidifying structure 26 may be configured as a mesh-like sheet or as a corrugated sheet of material made from, for example, nylon implanted or impregnated with silicone. At least a portion of the mesh-like or corrugated sheet may be attached to rigidifying bladder 14. (The dimensions for the components of stabilizer 10 in the drawings, for example, the thickness of the walls of bladders 12 and 14 are exaggerated for illustrative purposes.)

Referencing FIGS. 3A and 3A', exemplary bladder 14 is configured to be substantially flexible when suction is not applied at port 22, which is shown in FIG. 3A, and substantially rigid when suction is applied at port 22, which is shown in FIG. 3A'. As shown in FIG. 3A, inner chamber 24 has an ambient volume which provides space in which portions of rigidifying structure 26 may move with respect to each other, allowing bladder 14 to bend and flex. However, when suction is applied at port 22, negative pressure or a vacuum is induced within inner chamber 24, causing bladder 14 to collapse upon itself, as shown in FIG. 3A'. Inner chamber 24 now has a collapsed volume which is less than the ambient volume, and the space among rigidifying structure 26 is substantially reduced, thereby increasing the density of the rigidifying structure. Accordingly, individual portions of rigidifying structure 26 are urged together under pneumatic force and resist relative movement with respect to each other. As shown in the drawings, structure such as free-floating beads engage with spaces formed between attached beads to resist lateral movement relative to each other. If rigidifying structure 26 is configured as a mesh, then free-floating beans partially lodge within openings in the mesh. With the individual portions of rigidifying structure 26 urged together under vacuum to resist relative movement, collapsed bladder 14 is substantially inflexible, resists bending, and retains a stiffened position.

In this regard, a surgeon may apply and conform stabilizer 10 to tissue so that preferably a majority of the openings 20 contact or are incident on the tissue. Suction may be applied at port 16, causing suction to be applied at the openings 20 and thereby attaching stabilizer 10 to the tissue. Suction may then be applied at port 22 to stiffen or rigidify stabilizer 10, causing the stabilizer to maintain a desired position and configuration on the tissue. In applying exemplary stabilizer 10 to tissue in this matter, the surgeon may manipulate the tissue as desired by manipulating the stabilizer because the tissue is retained by the stabilizer. Accordingly, the retained tissue moves when the stabilizer moves or maintains a stabilized position when the stabilizer is motionless or anchored. A surgeon may then operate on the physically immobilized tissue without distraction or error caused by moving tissue.

Figure 3B:
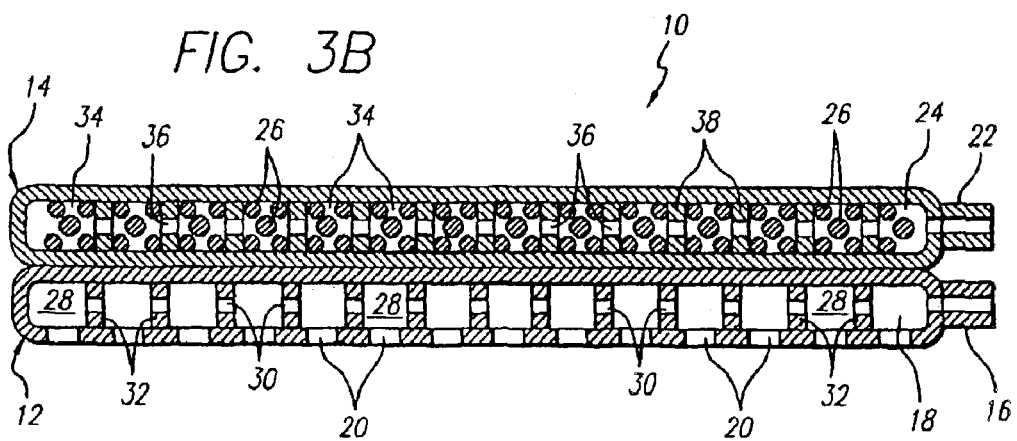
FIG. 3B is a cross-sectional view of the cardiac stabilizer taken along line 3—3 of FIG. 1, illustrating an alternative embodiment of the stabilizer.

An alternative embodiment of exemplary stabilizer 10 is illustrated in FIG. 3B. In this embodiment, exemplary attaching bladder 12 is configured so that inner chamber 18 is divided into a plurality of cells 28 which are connected by a plurality of air passages 30 formed through dividing walls 32. Each cell 28 may be elongate in shape, extending substantially from one side of bladder 12 to the other. Accordingly, each cell 28 may include a number of openings 20 disposed in a row along an extent thereof, such as illustrated in FIG. 2.

Also illustrated in FIG. 3B, exemplary rigidifying bladder 14 is configured so that inner chamber 24 is divided into a plurality of cells 34 which are connected by a plurality of air passages 36 formed through dividing walls 38. Each cell 34 of rigidifying bladder 14 may be elongate in shape, extending substantially from one side of bladder 14 to the other. Each cell 34 includes rigidifying structure 26 which may be disposed either attached to an inner wall of bladder 14 and/or dividing walls 38, free floating, or in a combination of both as shown in FIG. 3B. Free-floating rigidifying structure 26 may include spherical balls which are dimensioned to be larger than air passages 36 to prevent passage therethrough, as shown in FIG. 3B.

Another alternative embodiment of the tissue stabilizer of the present invention is illustrated in FIGS. 3C and 4. Rather than attaching bladders 12 and 14 in a substantially coplanar and coextensive relationship as shown in FIGS. 3A and 3B, attaching bladder 12 is imbedded within rigidifying bladder 14 in exemplary stabilizer 10 shown in FIGS. 3C and 4. In this embodiment, attaching bladder 12 includes a plurality of branching arms 40 which extend from a central channel 42. Each arm 40 provides a pneumatic conduit to a number of the openings 20 of attaching bladder 12, thereby providing communication for each opening 20 to port 16 via the inner chamber 18. Rigidifying bladder 14 exemplified in FIGS. 3C and 4 may include an inner wall 44 which separates the inner chamber 24 into two layers or sections. Wall 44 includes at least one air passage 46 so that each section of chamber 24 is in pneumatic communication with port 22. Rigidifying structure 26 may include attached as well as free-floating structure analogous to the description above. Although a single inner wall 44 is illustrated, rigidifying bladder 14 may include a plurality of walls 44 to separate inner chamber 24 into a plurality of sections or layers.

Referencing FIGS. 1 and 5, exemplary tissue stabilizer 10 of the invention may also include retaining structure 50 for engaging with external support apparatus. Exemplary retaining structure 50 may include a substantially rigid plate 52 and engaging structure 54. Plate 52 may be attached to either or both of the bladders 12 or 14 with, for example, adhesive or sewing. (Components of bladders 12 and 14 as described above are not shown in FIG. 5 for clarity.) Exemplary plate 52 may include a window 56 which provides a surgeon access to a surgical site on the tissue to which stabilizer 10 is attached. In the embodiment illustrated in the drawings, tissue stabilizer 10 and plate 52 have U-shape configurations, thereby defining window 56.

Although illustrated as a three-sided opening, exemplary window 56 may be four sided, that is, enclosed on all four sides. In addition, window 56 may be curvilinear (rather than rectilinear as shown) and may be offset from a medial axis of the tissue stabilizer (rather than centered as shown). Stabilizer 10 may be configured so that window 56 is wider at a top surface of the stabilizer and narrower at a bottom surface of the stabilizer, or vice versa. In addition, multiple windows 56 may be formed in the tissue stabilizer. In a multiple window embodiment, windows 56 may function as a vent for promoting or facilitating air circulation, which will be discussed in reference to alternative embodiments of the tissue stabilizer of the invention below.

Referencing FIG. 5A, the junction of rigid plate 52 and the bladders (either or both of bladders 12 and 14) may be configured at a stress-reducing section 57. For example, rigidifying bladder 14 may include rigidifying structure 26' configured as a flexible nylon mesh, and plate 52 may be made from a substantially rigid nylon, with section 57 being defined as an integral transition therebetween. Stress-reducing section 57 is more resilient than rigid plate 52 but less resilient than mesh 26', thereby allowing the mesh to flex with respect to the plate.

Exemplary engaging structure 54 may be configured as a ball 58 disposed on a post 60, with the post being attached to plate 52 and projecting away from the bladders 12 and 14. As shown in the drawings, engaging structure 54 includes a pair of balls 58 and posts 60. Balls 58 are configured to releasably engaging with complement external support structure, such as quick-release sockets with by a single flip lever operated with one hand as known in the art, which will be discussed in more detail below. Referring to FIG. 6, engaging structure 54 may include a plurality ball-and-post structures (58 and 60) arranged on tissue stabilizer 10. The plural balls 58 may be configured so that external support structure engages with at least two of the balls 58 simultaneously. As such, tissue stabilizer 10 is retained in a substantially rigid manner in all dimensions.

An alternative embodiment of the engaging structure of the present invention is illustrated in FIGS. 7, 8, and 9. Components of the alternative engaging structure 54' analogous to those shown in FIGS. 1 and 5 are reference with like numerals with the addition of a prime ('). Exemplary engaging structure 54' may include a cross bar 62 extending between a respective pair of posts 60' connected to rigid plate 52'. As shown in the drawings, a pair of cross bars 62 are provided. Each cross bar 62 is substantially rigid and provides an extended structure to which external support apparatus may be easily attached. When attached, tissue stabilizer 10 is pivotal only about a single axis, that is, the axis of the cross bar which is engaged with external structure. As particularly shown in FIG. 8, each cross bar 62 may have a polygonal cross section, for example, a hexagon.

FIG. 10 illustrates a preferred implementation of exemplary tissue stabilizer 10 of the present invention in which the stabilizer 10 stabilized the heart 70 during a surgical procedure. The heart 70 includes the left coronary artery 72 and the right coronary artery 74. The left coronary artery 72 includes the anterior descending branch 76 and the circumflex branch 78 which runs to the posterior side of the heart 70. In the example shown, the left coronary artery 72 has a diseased portion 80 which restricts the flow of oxygenated blood from the aorta 82. A coronary artery bypass grafting (CABG) procedure may be performed on the heart 70 to bypass the diseased portion 80. A coronary anastomosis is a CABG procedure which providing a graft 84 between the left coronary artery 72 and the internal mammary artery 86.

Figure 24:
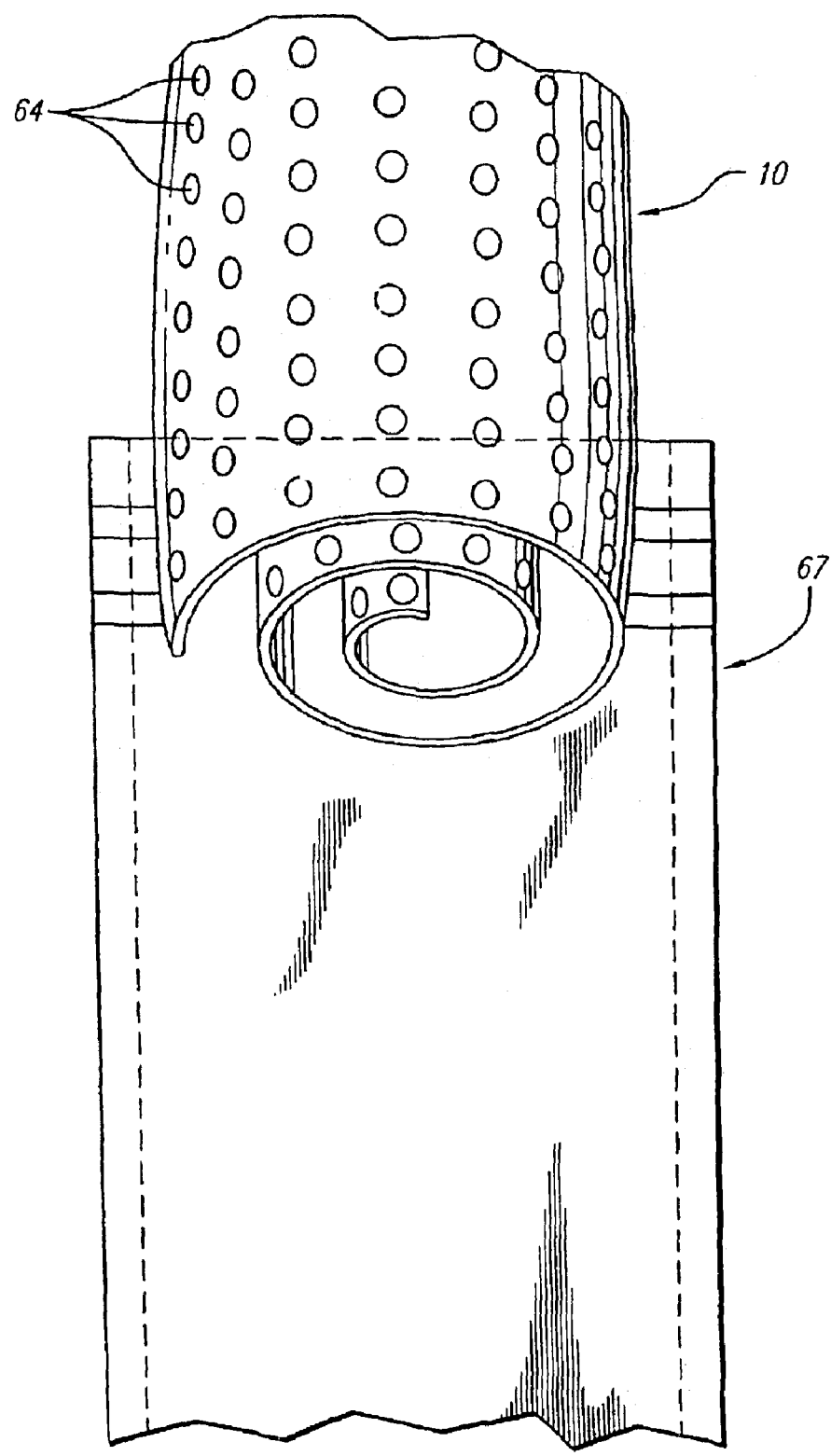
FIG. 24 is a schematic view of a tissue stabilizer of the present invention in use with a trocar sheath.

In order to perform a coronary anastomosis, a stable operating platform must be provided for the surgeon; that is, the heart 70 must be stabilized. This may be accomplished by placing the patient on a heart-lung machine and stopping the heart from beating with cardioplegia. Alternatively, coronary anastomosis may be performed on a heart which not stopped but which is warm and beating. Prior to utilizing the tissue stabilizer of the invention, access to the heart 70 is provided as known in the art, such as through a medial sternotomy or thoracotomy, which may also involve a retractor. Referring to FIG. 24, access may also be provided in a substantially minimally invasive manner, such as intercostally through a trocar sheath 67 or a "mini" thoracotomy.

In accordance with the present invention, stabilizer 10 may be applied to the heart 70 to stabilize the heart 70 at surgical site 88, thereby providing a stable operating platform for the surgeon. To perform CABG procedures with tissue stabilizer 10 of the invention, ports 16 and 22 of the stabilizer are connected to a source for suction, such as wall suction 90. Stabilizer 10 may include a pair of valves 92 and 94 for regulating the suction between the wall suction 90 and ports 16 and 22, respectively. Cardiac stabilizer 10 may then be positioned on the epicardium of the heart 70, with window 56 positioned to provide access to the surgical site 88. As shown, the coronary artery 72 is positioned within window 56. When in a desired position, suction may be applied at port 16 of the attaching bladder by, for example, actuating valve 92, thereby attaching or securing the stabilizer to the epicardium of the heart 70.

The suction applied to port 16 is at a level which minimizes or substantially prevents trauma to the epicardium. Depending upon the configuration of attaching bladder 12, such as the size and/or number of openings 20, the level of applied suction may range from, for example, about 50 millimeters of mercury (mm Hg) to about 150 mm Hg. This pressure range may be at the lower end of the scale if a relatively large number of openings 20 are provided and at the higher end of the scale if a relatively small number of openings 20 are provided.

The applied suction may attach stabilizer 10 to the heart 70 with a level of force which allows the stabilizer to be moved or slid across the tissue under hand pressure. This feature facilitates the positioning of stabilizer 10 to a desired location. It also enables flexible stabilizer 10 to be contoured to the anatomical topography of the heart 70, providing optimal contact or incidence of the openings 20 on the surface of the epicardium. As shown in FIG. 10, stabilizer 10 conforms to the left ventricle much like a patch, substantially "wrapping" around a portion thereof. The U-shape configuration of stabilizer 10 allows the surgeon to place a hand on the stabilizer with his or her fingers straddling window 56, which ergonomically facilitates the positioning and contouring thereof. Only one hand is need to position the cardiac stabilizer on the heart.

Once contoured and positioned as desired, suction may be applied at port 22 of rigidifying bladder 14 by, for example, actuating valve 94, thereby stiffening stabilizer 10 and maintaining the desired contour. The suction applied at port 22 is at a level which retards bending and flexing of stabilizer 10 under hand pressure. Depending upon the configuration of rigidifying bladder 14, such as the size and/or number of free-floating rigidifying structures 26, the level of suction applied at port 22 may range from, for example, about 80 mm Hg to about 120 mm Hg. For many cardiac applications, the suction applied to port 22 is such that stabilizer 10 is rigid to about 5 pounds to 10 pounds of force.

Once suction is applied to both ports 16 and 22 as described above, stabilizer 10 is attached and rigid, with the heart 70 being in its normal cardiac anatomical position. The tissue of the heart 70 to which cardiac stabilizer 10 is attached is stabilized, as well as the coronary artery 72 positioned within window 56. Stabilizer 10 may then be raised, thereby also raising the heart 70 to a position at which the coronary anastomosis may be best performed. Once the heart 70 is in a desired anastomosis position, stabilizer 10 may be attached to external support structure 96 to retain the stabilizer and, therefore, the heart 70 in the anastomosis position.

External support structure 96 may include an articulated arm 98 with a socket 100, preferably a quick-release socket as shown, which is releasably engageable with ball 58 of stabilizer 10. Although a ball-and-socket arrangement is used for the purposes of this description, any complementary releasable fastening means may be implemented. External support structure 96 may include a sternal retractor 102 or a bed post 104 to which support arm 98 is attachable. Articulated support arm 98 may bendable under sufficient hand force. Alternatively, arm 98 may be substantially flexible for positioning and then made rigid through the use of a tensioning cable mechanism, as known in the art. Although only one support arm 98 is shown, external support structure 96 may include a second support arm attached to the second ball-and-post arrangement (58 and 60) of stabilizer 10. Once stabilizer 10 is retained by the external support structure 96, the heart 70 is in a stable position and the coronary anastomosis may be performed.

In certain patients, when the heart 70 is moved form the normal cardiac anatomical position to the anastomosis position, hemodynamic instability may occur and threaten the health of the patient. To stop the hemodynamic instability, the heart 70 needs to be returned to the cardiac anatomical position, preferably in an expedient manner. In accordance with the present invention, tissue stabilizer 10 may be released from external support structure 96 by disengaging quick-release socket 100 from ball 58, allowing the stabilizer and the heart 70 to be moved and lowered to the cardiac anatomical position. After the heart 70 has recovered, stabilizer 10 may be raised to replace the heart 70 in the anastomosis position, as described above. This quick-release feature of the invention is particularly useful if the coronary anastomosis is being performed on the circumflex branch 78 of the left coronary artery 72. To perform such a procedure, the heart 70 needs to be lifted and/or rotated to a substantial degree out of the normal cardiac anatomical position to provide access to the circumflex branch 78 which is located at the posterior of the heart 70.

Returning to the level of suction applied to attaching bladder 12, if the coronary anastomosis is performed on the anterior descending branch 76 of the coronary artery 72, then the heart 70 does not need to be moved a substantial degree to provide access to the surgical site 88. However, if the coronary anastomosis is performed on the circumflex branch 78 of the coronary artery 72, then the heart 70 needs to be moved or rotated a substantial degree to provide access to the surgical site. As the heart 70 may weigh about eight pounds in an average human, a substantial amount of force is required to maintain the heart 70 in the desired anastomosis position. Accordingly, the level of suction applied to port 16 to attach stabilizer 10 to the heart 70 may be higher when coronary anastomosis is performed on the circumflex branch 78 than when performed on the anterior descending branch 76. For example, about 100 mm Hg to about 200 mm Hg may be applied to port 16 in the case of the circumflex branch 78, and about 50 mm Hg to about 150 mm Hg may be applied to port 16 in the case of the anterior descending branch 76. For more specific values, these exemplary ranges may be limited to about 120 mm Hg in the circumflex instance and about 80 in the anterior descending instance. In addition, the combination of level of applied suction and the number and/or size of the openings 20 may be configured to retain up to about 25 pounds of force that the heart 70 may apply when moved to provide access to the circumflex branch 78 of the coronary artery 72. Similarly, the external support structure 96, particularly socket 100 may be configured to tolerate up to about 50 pounds or more of force.

During the coronary anastomosis, the heart 70 may be repositioned as desired by bending or repositioning articulated arm 98. Alternatively, the heart 70 may be repositioned by releasing stabilizer 10 from support arm 98, repositioning the stabilizer and heart as desired, and then reattaching the stabilizer to the arm. After the coronary anastomosis is completed, stabilizer 10 may be detached from the external support structure 96, allowing the heart 70 to be returned to the normal cardiac anatomical position. The suction may then be disconnected from ports 16 and 22 by actuating valves 92 and 94. Accordingly, stabilizer 10 becomes flexible and unattached to the heart 70 and may be removed. As many patients require more than one bypass to be performed, the surgeon may then reapply stabilizer 10 to another portion of the heart 70 to performed another CABG procedure, such as on the right coronary artery 74, in the manner described above. This reapplying of the stabilizer 10 may continued a plurality of times to perform as many CABG are necessary for the patient.

In a commercial medical embodiment of tissue stabilizer 10, bladders 12 and 14 may be made from substantially pneumatically impervious and biocompatible material such as silicone or rubber. Rigidifying structure 26 may be made from silicone or epoxy material or from metal and may include free-floating metal or epoxy beads. Rigidifying structure 26 may also me made from nylon-reinforced silicone mounted to bladder 14. Retaining structure 54 may be made for stainless steel or other suitably rigid material such as nylon.

The overall dimensions of stabilizer 10 configured for cardiac use may be about 10 centimeters (cm) to about 15 cm in width and length and may be about 0.5 cm to about 2 cm in thickness. Window 56 may be about 0.5 cm to about 2 cm in width and at least about 3 cm in length. Openings 20 may be about 0.25 cm to about 1 cm in diameter. Ball 58 may have a diameter of about 0.5 cm to 1 cm and may project above a top surface of stabilizer 10 by about 0.75 cm to about 3 cm.

The foregoing description of the present invention focused on exemplary tissue stabilizer 10 for cardiac applications. However, as previously mentioned, the tissue stabilizer of the present invention may be configured in accordance with many other applications. Broadly speaking, the teachings of the present invention are applicable to any situation which requires tissue stabilization. As will be described below, the tissue stabilizer of the present invention may be configured to stabilize, for example, an injured neck, a broken leg or arm, and a sprained wrist or foot. Those skilled in the art will appreciate any number of additional applications of the tissue stabilizer from the teachings herein.

Figure 11:
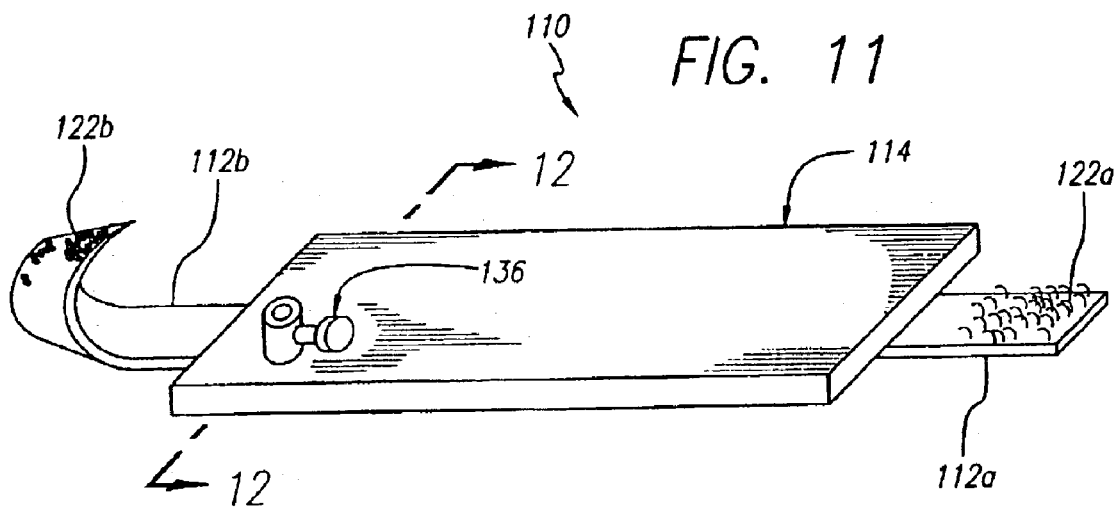
FIG. 11 is a perspective view of a tissue stabilizer configured in accordance with the present invention.

In this regard, FIG. 11 illustrates a tissue stabilizer 110 which includes flexible complementary straps 112 and a flexible rigidifying bladder 114 attached to the straps. As a referencing convention herein, straps are generally referenced by numeral 112 and specifically referenced with an alpha suffix 112a and 112b, which convention will be used analogously for other elements of the invention. With additional reference to FIGS. 12A and 12B, analogous to the cardiac tissue stabilizer described above, rigidifying bladder 114 of exemplary tissue stabilizer 110 includes an inner chamber 116 defined therein and a port 118 in communication with chamber 116 and through which the chamber may be evacuated. Exemplary rigidifying bladder 114 also includes rigidifying structure 120 disposed within chamber 116 which is configured to be substantially flexible when the chamber is at ambient pressure or not evacuated, as shown in FIG. 12A, and substantially rigid when the chamber is evacuated through port 118 or under vacuum, as shown in FIG. 12B. When rigidified, tissue stabilizer 110 provides substantially rigid support to tissue.

Similar to attaching bladder 12 of the cardiac stabilizer described above, flexible straps 112 provide a means for attaching rigidifying bladder 114 to tissue to be stabilized. For example, with reference to FIG. 15 in which tissue stabilizer 110 is configured for application to a leg, once flexible rigidifying bladder 114 is positioned and wrapped around the leg, straps 112 attach and secure the rigidifying bladder in place. Each strap 112a and 112b may include complementary fastening means for releasably securing the straps together, such as hooks 122a and eyes 122b (for example, Velcro®). Exemplary tissue stabilizer 110 may include a plurality of complementary pairs of straps 112, which will be discussed below.

Alternatively, straps 112 may include adhesive for releasably securing the straps together. As shown in FIG. 13, strap 112a may include pressure-sensitive adhesive 124, and strap 112b may include a tab 126 to which pressure-sensitive adhesive 124 is adherent. And as shown in FIG. 14, strap 112a may include cohesive adhesive 128a, and strap 112b may include cohesive adhesive 128b which is complementary to adhesive 128a. As known in the art, cohesive adhesives are only adherent when in contact with each other but are not tacky to human touch. In addition to the hook-and-eye fasteners (122) and the adhesive (124 and 128), other fastening means may be used such as snaps, buckles, and so on. Flexible straps 112 may be made from elastic or inelastic material, depending upon the application.

Figure 16:
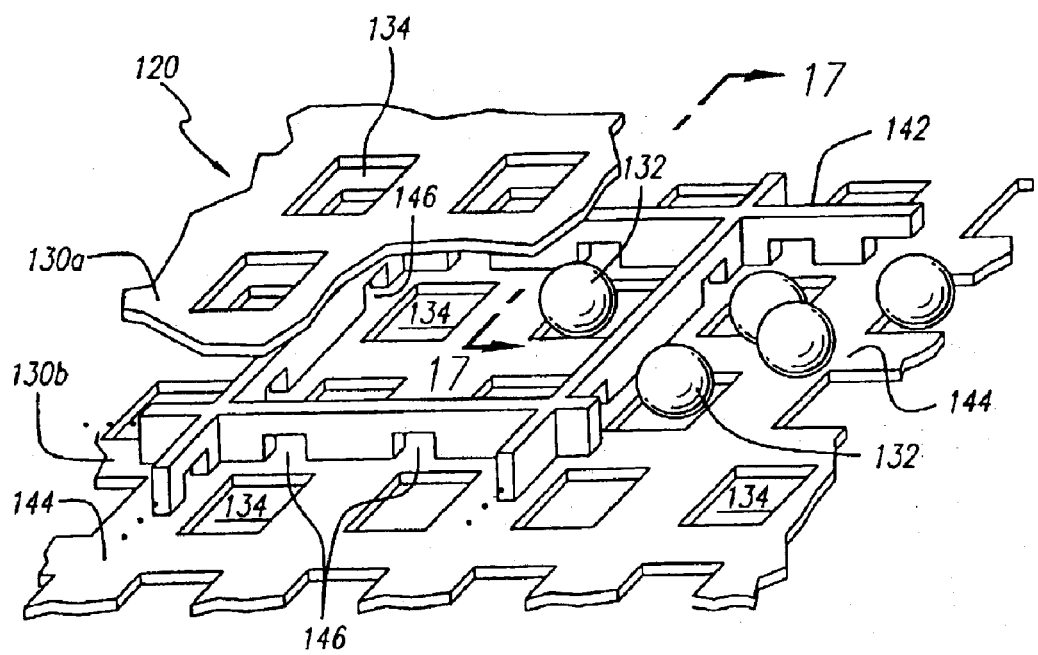
FIG. 16 is a perspective view of exemplary rigidifying structure of the tissue stabilizer of the present invention.

Referencing FIGS. 12A, 12B, and 16, exemplary rigidifying structure 120 may include mesh 130 attached to bladder 114 and a plurality of movable beads 132. Chamber 116 is preferably configured with opposing layers of mesh, referenced as 130a and 130b, between which a plurality of beads 132 are disposed. When chamber 116 is at ambient pressure (i.e., not evacuated or under vacuum), rigidifying bladder 114 and, accordingly, tissue stabilizer 110 are flexible, as shown in FIG. 12A. However, when chamber 116 is evacuated through port 118, rigidifying bladder 114 collapses under the negative pressure, drawing opposing layers of mesh 130a and 130b together. Beads or balls 132 lodge within recesses 134 in mesh 130 and are urged therein under the applied negative pressure, thereby rigidifying the bladder, as shown in FIG. 12B. Rigidifying bladder 114 may include a valve 136 disposed over port 118 which may be closed to retain the vacuum of chamber 116, thereby retaining the rigidity of bladder 114.

Rigidifying bladder 114 may include a plurality of walls 138 which separate inner chamber 116 into a plurality of layers. Each layer may be in pneumatic communication via air passages 140 formed through walls 138. Generally speaking, the more layers that rigidifying bladder 114 has, the more rigid the bladder becomes under vacuum. Each of the layers may include a pair of opposing layers of mesh 130a and 130b, as well as a plurality of movable beads 132, as shown in FIGS. 12A and 12B. The increased rigidity results from the increased number of beads 132 which may be provided to lodge and engage with multiple sheets of mesh 130. The applied negative pressure increases the frictional forces between the plurality of beads 132 and the mesh 130, as well as between each other, which resists flexing and movement.

With particular reference to FIG. 16, rigidifying structure 120 may include a plurality of dividing walls 142 extending between opposing layers of mesh 130a and 130b, thereby dividing each layer of inner chamber 116 into a plurality of cells 144. Dividing walls 142 include at least one air passage 146 for providing pneumatic communication between adjacent cells 144. Dividing walls 142 retain a predetermined number of movable beads 132 within each cell. Generally speaking, dividing walls 142 prevent the migration of substantial numbers of the beads to one end of rigidifying bladder, thereby ensuring a consistent level of rigidity across the extent of the bladder. To prevent the obstruction of air through port 118 and air passages 140 and 146, beads 132 may be multifaceted or oversized to prevent an air-tight seal from being formed if a bead lodges in the port or one of the air passages. Alternatively, beads 132 may include holes formed therethrough to allow the passage of air.

The dividing walls 142 are preferably collapsible to allow opposing layers of mesh 130a and 130b to be drawn together (see FIG. 12B). In this regard, walls 142 may be made from a substantially resilient material such as foam rubber which provides support when chamber 116 is at ambient pressure, as shown in FIG. 17A, and which compresses and collapses when chamber is at negative pressure, as shown in FIG. 17B. Alternatively, dividing walls 142 may include a pivot point 148 as shown in FIG. 18 or a reduced-thickness area or crease 150 as shown in FIG. 19 to facilitate the collapse or compression of walls 142.

Figure 20:
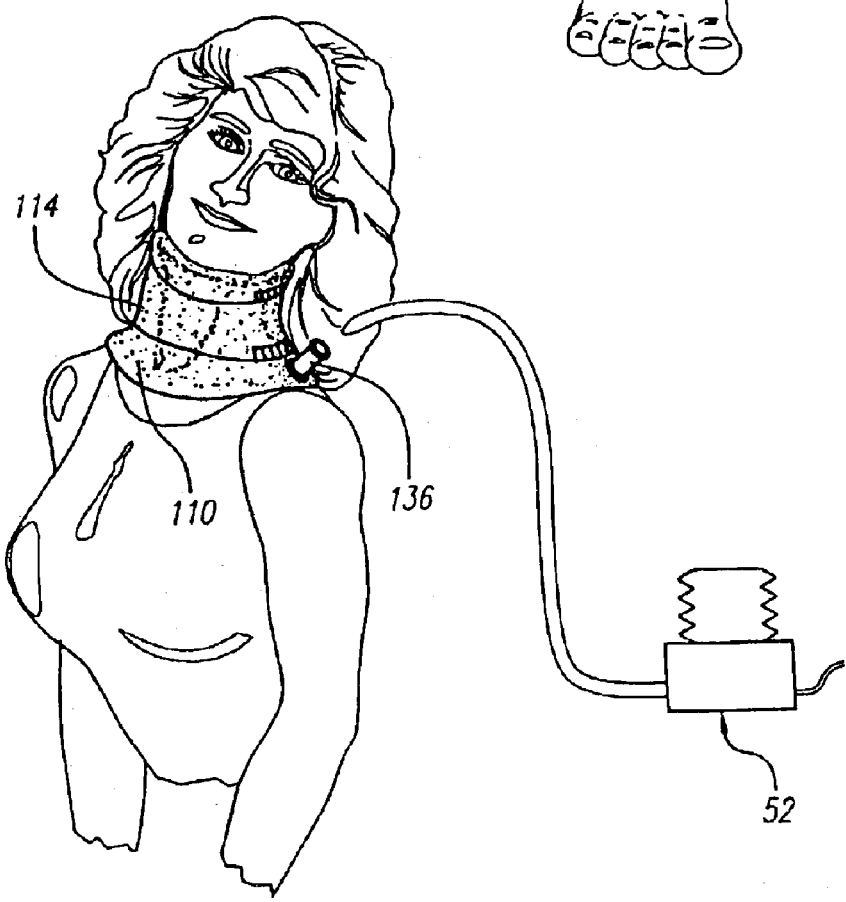
FIG. 20 is a schematic view of the tissue stabilizer of the present invention configured for use in stabilizing a neck.

As mentioned above, the tissue stabilizer of the present invention may be configured to satisfy a wide range of applications. As already mentioned in reference to FIG. 15, tissue stabilizer 110 may be configured to stabilize an injured leg, for example, a broken leg. Referencing FIG. 20, exemplary tissue stabilizer 110 is configured to provide support and stabilize the neck of an injured person. In this embodiment, tissue stabilizer 110 may be carried by emergency rescue teams to remote locations for use in stabilizing potential victims of neck and spinal injuries. At remote locations, a portable pump 152 may be engaged with valve 136 and actuated to evacuate chamber 116 to rigidify bladder 114. Portable pump 152 may be of the type analogous to those used for inflating blood-pressure cuffs. Whereas conventional neck braces are manufactured in standard sizes which might not fits all patients, tissue stabilizer 110 of the present invention may be contours to fit the neck of each individual patient, thereby providing much better support and stability.

Figure 15:
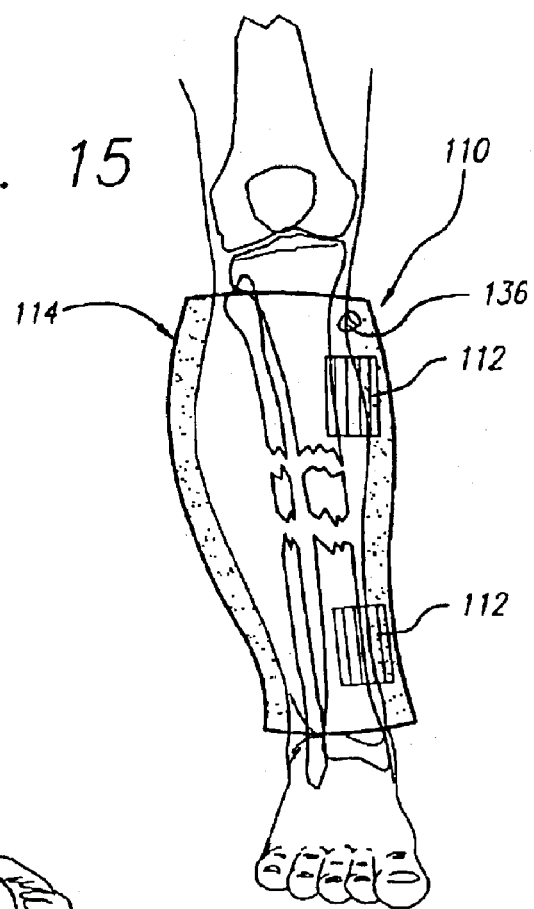
FIG. 15 is a schematic view of the tissue stabilizer of the invention configured for use with a leg.
Figure 21:
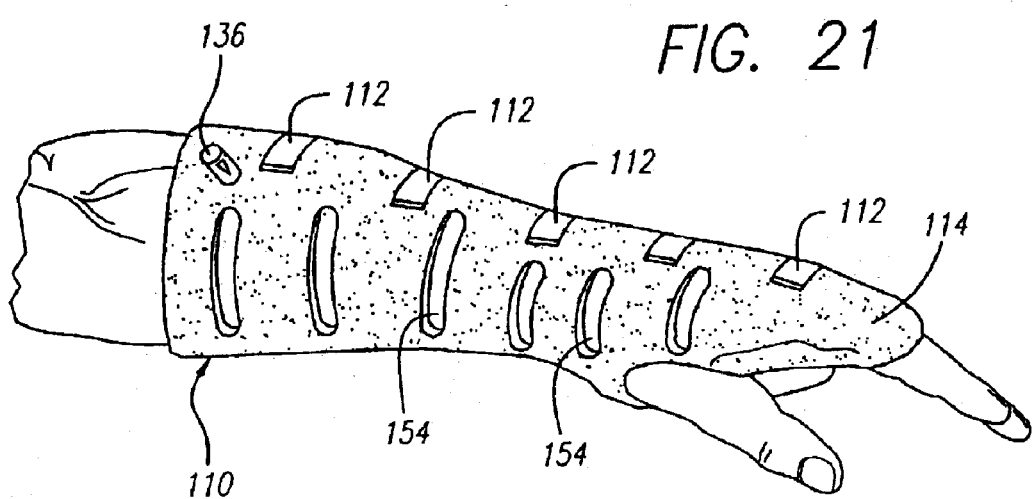
FIG. 21 is a schematic view of the tissue stabilizer of the invention configured for use in stabilizing an arm.

Exemplary tissue stabilizer 110 may be configured to stabilize a sprained wrist or broken arm, as illustrated in FIG. 21. In this embodiment, tissue stabilizer 110 may include a plurality of complementary pairs of straps 112 for attaching rigidifying bladder 114 to the arm. In the case where a bone is broken (as shown in FIG. 15), tissue stabilizer 110 may serve as a cast, replacing conventional plaster or fiberglass casts. A doctor may set the broken bone and then apply the tissue stabilizer 110 in accordance with the foregoing description. The bone may be X-rayed to determine the integrity of the set. If the bone was set unsatisfactory, tissue stabilizer 110 may be removed as described above, and the bone may be reset; thereafter, the tissue stabilizer may be reattached to the tissue and re-rigidified.

In addition to this temporary stabilization embodiment, tissue stabilizer 110 may be also configured to provide semi-permanent or permanent stabilization for tissue. For example, an additional access port (not shown) may be formed in rigidifying bladder 114 through which adhesive, such as epoxy or glue, may be provided to fix the movable beads 132 to mesh 130. The adhesive may be injected through the additional access port or may be drawn into and dispersed throughout chamber 116 under suction on port 118. Accordingly, once the adhesive sets, tissue stabilizer 110 will retain a desired shape and stabilize tissue even if chamber 116 loses a portion or all of the negative pressure by, for example, pneumatic leakage through valve 136.

As shown in FIG. 21, tissue stabilizer 110 may include a plurality of vents 154 formed through bladder 114 to provide air circulation to the skin and relief to the patient. Vents 154 may be in the form of small perforations formed through the bladder, and may be formed analogously to window 56 described above (see FIG. 1). In addition, tissue stabilizer 110 may be made from material such as silicone and nylon which may be exposed to water without adverse effects (as opposed to plaster casts), allowing a user to conveniently bath and allowing a user to clean the tissue stabilizer if soiled.

Figure 22:
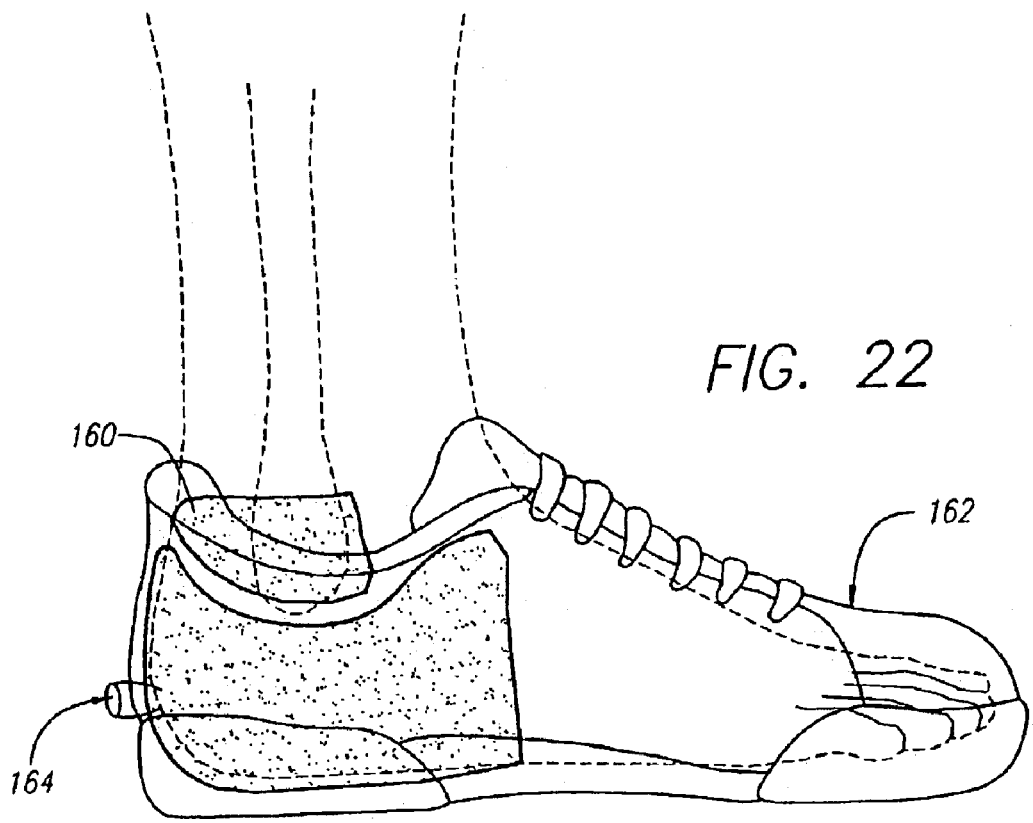
FIG. 22 is a schematic view of a shoe in accordance with the invention in which the tissue stabilizer is configured as a liner for providing heel fit and/or ankle support.

Another exemplary embodiment of the tissue stabilizer of the present invention is illustrated in FIG. 22, which is referenced by numeral 160. In this embodiment, tissue stabilizer 160 is configured to be incorporated into footwear, such as an athletic shoe 162. Many athletic shoes attempt to support a user's ankle to prevent injury. Athletic shoe 162 of the present invention supports the ankle by including tissue stabilizer 160 which may be configured like a sock or a shoe liner to fit around a user's heel and/or ankel. Tissue stabilizer 160 includes a valve 164 through which rigidifying bladder (not shown) may be deflated or evacuated and for sealing the bladder. In addition to athletic shoes such as basketball shoes, the tissue stabilizer of the invention may be incorporated into skates (both in-line and ice), ski boots, hiking shoes, and so on. Alternatively, tissue stabilizer may be configured as an insole so that when rigidified, the stabilizer serves as an orthotic device.

In addition to the numerous applications described above, the teachings of the present invention may be applied to other tissue supporting or stabilizing situations. In this regard, those skilled in the art will appreciated that the tissue stabilizer may be modified for use in augmentation and cosmetic surgery, for example, in connection with penile implants or breast implants, without departing from the teachings of the present invention. Also, tissue stabilizers may be configured to support organs other than the heart described above. For example, to control a hemorrhage in an organ such as the liver or the spleen, the tissue stabilizer may be wrapped about the organ to provide support. In such a hemorrhage control embodiment, the tissue stabilizer may include a collagen layer to facilitate homeostasis. Tissue stabilizer may also be configured for use in support and stabilizing prosthetics by providing a connective interface between the prosthetic and the bone to which it is connected. Furthermore, tissue stabilizer may be incorporated into protective clothing use in sport, for example, shin and chest guards, helmets, gloves, and so on. In these embodiments, the tissue stabilizer may include a layer of padding material to provide cushion or shock absorbency between the tissue to be protected and the rigid bladder.

As previously mentioned, the rigidifying bladder may be made from silicone impregnated with nylon (with the nylon comprising at least a portion of the rigidifying structure). The rigidifying bladder may be include natural fibers such as cotton (e.g., canvas) or metallic fibers such as stainless-steel mesh to provide durability. Alternatively, tissue stabilizer may be made from substantially resilient material, such as certain silicones, so as to stretch under sufficient force. In addition, rather than pneumatic evacuation of rigidifying bladder of the invention, fluids other than air, such as hydraulics may be used. As an alternative means for attaching the rigidifying bladder to tissue, rather than including straps 112, tissue stabilizer 110 may include a layer of adhesive coated onto one side of the rigidifying bladder 114 with a peel-away backing.

The layer of adhesive may be adhered directed to the skin of the patient or to a layer of pre-wrap (as known in the art).

Those skilled in the art will understand that the preceding exemplary embodiments of the present invention provide the foundation for numerous alternatives and modifications thereto. These other modifications are also within the scope of the present invention. For example, in addition to stabilizing human tissue in medical applications, the tissue stabilizer of the present invention may be configured to stabilize other animal tissue in veterinarian applications and plant tissue in botanical applications. Other applications in which the stabilizer may provide temporary rigid support is in the building and construction industry. In this case, the stabilizer may be configured to be much larger than that described above and much more durable to withstand hazardous working conditions. Accordingly, the present invention is not limited to the embodiments precisely shown and described above.

We claim:

1. A method for positioning a beating heart, said method comprising:

placing a cardiac stabilizer on an epicardium of the beating heart;

applying a vacuum to the stabilizer to contour the stabilizer to a surface topography of the epicardium of the beating heart;

applying a vacuum to rigidify the stabilizer;

moving the beating heart with the stabilizer from the anatomical position to the anastomosis position while the heart remains securely retained by the stabilizer.

2. A method as in claim 1, wherein the cardiac stabilizer is positioned through a sternotomy.

3. A method as in claim 1, wherein the stabilizer is positioned through a thoracotomy.

4. A method as in claim 1, wherein the stabilizer is positioned intercostally through a sheath.

5. A method as in claim 1, further comprising anchoring the stabilizer to an external support structure after the beating heart has been moved to a desired position.

6. A method as in claim 1, further comprising monitoring hemodynamic stability of the heart and returning the heart to the anatomical position if hemodynamic instability is observed.

7. A method for temporarily stabilizing tissue comprising:

providing a conformable tissue stabilizer including:
a rigidifying bladder component;
a port through which said bladder is evacuatable; and
vacuum attaching means for applying a vacuum for securing said rigidifying bladder to tissue;

positioning said tissue stabilizer on tissue to be stabilized;

attaching said tissue stabilizer to the tissue with said attaching means; and rigidifying said tissue stabilizer by applying suction at said port.

8. A method for stabilizing tissue as claimed in claim 7, further comprising the de-rigidifying said tissue stabilizer.

9. A method for stabilizing tissue as claimed in claim 7, further comprising detaching said tissue stabilizer from the tissue.

10. A method for stabilizing tissue as claimed in claim 7, wherein said rigidifying and attaching steps are facilitated by applying suction through a suction apparatus comprised of the a second bladder bladder, the suction apparatus configured to be attached to tissue for stabilization, the suction apparatus facilitating creation of sub-atmospheric pressure between tissue and the suction apparatus, enabling attachment of said conformable tissue stabilizer to tissue.

* * * * *